(12) United States Patent
Yogi et al.

(10) Patent No.: US 6,881,587 B2
(45) Date of Patent: Apr. 19, 2005

(54) LIQUID-CONTAINING SUBSTANCE ANALYZING DEVICE AND LIQUID-CONTAINING SUBSTANCE ANALYZING METHOD

(75) Inventors: Osamu Yogi, Hamamatsu (JP); Tomonori Kawakami, Hamamatsu (JP); Mitsuru Ishikawa, Tsukuba (JP)

(73) Assignee: Hamamatsu Photonics K.K., Shizuoka (JP)

( * ) Notice: Subject to any disclaimer, the term of this patent is extended or adjusted under 35 U.S.C. 154(b) by 188 days.

(21) Appl. No.: 10/344,265
(22) PCT Filed: Aug. 10, 2001
(86) PCT No.: PCT/JP01/06938

§ 371 (c)(1),
(2), (4) Date: Feb. 10, 2003

(87) PCT Pub. No.: WO02/14842
PCT Pub. Date: Feb. 21, 2002

(65) Prior Publication Data
US 2003/0170732 A1 Sep. 11, 2003

(30) Foreign Application Priority Data
Aug. 11, 2000 (JP) ........................................ 2000-244643

(51) Int. Cl.⁷ .............................................. G01N 21/64
(52) U.S. Cl. ....................... 436/172; 436/174; 436/180; 422/63; 422/67; 422/82.08
(58) Field of Search .......................... 422/82.05, 82.08, 422/82.09, 63, 67, 119; 436/172, 174, 180; 356/72, 73

(56) References Cited

U.S. PATENT DOCUMENTS

| | | | |
|---|---|---|---|
| 4,934,811 A | * 6/1990 | Watts et al. | 356/73 |
| 5,141,871 A | * 8/1992 | Kureshy et al. | 436/47 |
| 5,270,210 A | * 12/1993 | Weyrauch et al. | 436/43 |
| 5,494,829 A | * 2/1996 | Sandstrom et al. | 436/518 |
| 5,528,046 A | 6/1996 | Ishikawa | 250/461.2 |
| 5,760,900 A | 6/1998 | Ito et al. | 356/338 |
| 5,965,446 A | 10/1999 | Ishikawa | 436/5 |
| 6,071,748 A | * 6/2000 | Modlin et al. | 436/174 |
| 6,228,652 B1 | * 5/2001 | Rodriguez et al. | 436/63 |
| 6,284,465 B1 | * 9/2001 | Wolber | 435/6 |
| 6,466,316 B1 | * 10/2002 | Modlin et al. | 356/318 |

FOREIGN PATENT DOCUMENTS

| | | |
|---|---|---|
| EP | 0 780 679 A2 | 6/1997 |
| JP | 6-148076 A | 5/1994 |
| JP | 10-185782 A | 7/1998 |
| JP | 2000111404 | 4/2000 |
| JP | 2000-111477 | 4/2000 |

* cited by examiner

Primary Examiner—Jeffrey R. Snay
(74) Attorney, Agent, or Firm—Morgan Lewis & Bockius LLP

(57) ABSTRACT

A liquid-contained substance analysis device according to this invention comprises: a substrate 14, which is coated on the surface with PVA and which is mirror finished; a first light source 18 for illuminating light onto substrate 14; and light detector 30, which detects the scattered light due to a liquid or a trace of a liquid that exists on substrate 14, and the position of liquid L or trace of liquid L is detected based on the scattered light detected by light detector 30. By then illuminating excitation light from a second light source 20 onto the detected position, the substances contained in liquid L are analyzed.

6 Claims, 6 Drawing Sheets

LIQUID-CONTAINING SUBSTANCE ANALYZING DEVICE AND LIQUID-CONTAINING SUBSTANCE ANALYZING METHOD

TECHNICAL FIELD

This invention concerns a liquid-contained substance analysis device and a liquid-contained substance analysis method for analyzing substances contained in a liquid, and particularly concerns those used for analysis of microvolumes of liquid.

BACKGROUND ART

Arts for analyzing substances contained in a liquid have existed since priorly. As methods for specifying the position of a liquid that is analyzed in such analysis of liquid-contained substances, methods of using microtiter plates and methods, in which markers for positioning are prepared in advance on a substrate onto which a liquid is to be dropped, have been known.

DISCLOSURE OF THE INVENTION

However, the abovementioned methods of specifying the position of a liquid had the following problems due to degradation of the positional precision of the dropping of liquid as the quantity of liquid to be analyzed became minute. That is, present microtiter plates are not suitable for realizing high densities and, to begin with, cannot be applied to microvolumes of liquid. With methods in which markers for positioning are prepared in advance on a substrate onto which a liquid is to be dropped, since accurate dropping of a microvolume of the liquid onto the position at which a marker has been made was difficult, it was difficult to ascertain onto which position on the substrate the liquid had been dropped.

Furthermore when the quantity of liquid is extremely minute, the liquid evaporates readily, and with types of liquid that evaporate immediately upon being dropped onto a substrate, the position of liquid was even more difficult to ascertain.

An object of this invention is thus to resolve the above problems and to provide a liquid-contained substance analysis device and a liquid-contained substance analysis method, which enable the positions of microvolumes of liquid to be ascertained smoothly and thereby enable substances contained in the liquid to be analyzed readily.

A liquid-contained substance analysis device according to this invention comprises: a mirror-finished substrate, onto which a liquid that is to be analyzed is dropped; a first light source for illuminating the substrate; a light detector, detecting scattered light resulting from the scattering of light from the first light source by the liquid or trace of the liquid that has been dropped onto the substrate; a position detector, detecting the position onto which the liquid has been dropped based on the scattered light detected by the light detector; a second light source, illuminating the position detected by the position detector with light of a shorter wavelength than the light output from the first light source; a fluorescence detector, detecting fluorescence resulting from the excitation of the liquid or trace of the liquid by the light that has been illuminated from the second light source; and an analyzer, analyzing substances contained in the liquid by the fluorescence detected by the fluorescence detector.

By thus illuminating light onto the mirror-finished substrate and using the resulting scattered light from the liquid or trace of the liquid that exists on the substrate, the position at which the liquid exists can be detected readily. That is, since the mirror-finished substrate will not give rise to scattered light, it can be judged that the liquid or trace of the liquid exists when scattered light occurs. By then illuminating light from the second light source onto the position at which the liquid or trace of the liquid has been detected and analyzing the fluorescence emitted by excitation of the substances contained in the liquid, the substances contained in a microvolume of liquid can be analyzed smoothly.

With the above-described liquid-contained substance analysis device, the second light source may be positioned so that the output light from the second light source intersects the normal to the substrate plane and the fluorescence detector may be positioned in the direction of the normal to the substrate plane.

By thus making the light output from the second light source be incident so as to intersect the direction of the normal to the substrate plane and detecting the fluorescence excited by this light by means of a fluorescence detector positioned in the direction of the normal to the substrate plane, the reflected light output from the second light source will be prevented from becoming incident directly onto the fluorescence detector, thereby enabling a weak fluorescence to be detected.

Also with the above-described liquid-contained substance analysis device, the surface of the substrate may be coated with a water-soluble organic thin film.

When the substrate is coated with a water-soluble organic thin film, the substrate surface becomes modified at apart at which a liquid has been dropped, thereby enabling the trace of the liquid to be detected even when the liquid evaporates.

Also with the above-described liquid-contained substance analysis device, the substrate may be a silicon substrate on which a natural oxidation film has been formed.

When such a silicon substrate, on which a natural oxidation film has been formed, is used, the substrate surface of a portion on which a liquid has been dropped becomes modified by the formation of a new silicon oxide film, thereby enabling the trace of the liquid to be detected even when the liquid evaporates.

The above-described liquid-contained substance analysis device may furthermore be equipped with a stage for setting the substrate thereon and moving the substrate so that light from the first light source will be illuminated onto the substrate.

By thus placing the substrate on the stage and making the substrate movable, the illumination positions of the light output from the first light source and second light source that illuminate the substrate can be shifted.

A liquid-contained substance analysis method according to this invention comprises: a liquid dropping step of dropping a liquid to be analyzed onto a mirror-finished substrate; a light illumination step of illuminating light onto the substrate by means of a first light source; a scattered light detection step of detecting scattered light resulting from the scattering of light from the first light source by the liquid or trace of the liquid that has been dropped onto the substrate in the liquid dropping step; a position detection step of detecting the position onto which the liquid has been dropped based on the scattered light detected in the scattered light detection step; a second light illumination step of illuminating the position detected in the position detection step with light from a second light source that outputs light of a shorter wavelength than the light output from the first light source; a fluorescence detection step of detecting the fluorescence resulting from the excitation of the liquid or trace of the liquid by the light illuminated in the second light illumination step; and an analysis step of analyzing substances contained in the liquid based on the fluorescence detected in the fluorescence detection step.

By thus illuminating light onto the mirror-finished substrate and using the resulting scattered light from the liquid or trace of the liquid that exists on the substrate, the position at which the liquid exists can be detected readily. That is, since the mirror-finished substrate will not give rise to scattered light, it can be judged that the liquid or trace of the liquid exists when scattered light occurs.

By then illuminating light from the second light source onto the position at which the liquid or trace of the liquid has been detected and analyzing the fluorescence emitted by excitation of the substances contained in the liquid, the substances contained in the microvolume of liquid can be analyzed smoothly.

BEST MODES FOR CARRYING OUT THE INVENTION

Preferred embodiments of liquid-contained substance analysis devices according to this invention shall now be described in detail along with the drawings. With regard to the description of the drawings, the same elements shall be provided with the same symbols and redundant explanations shall be omitted.

Figure 1:
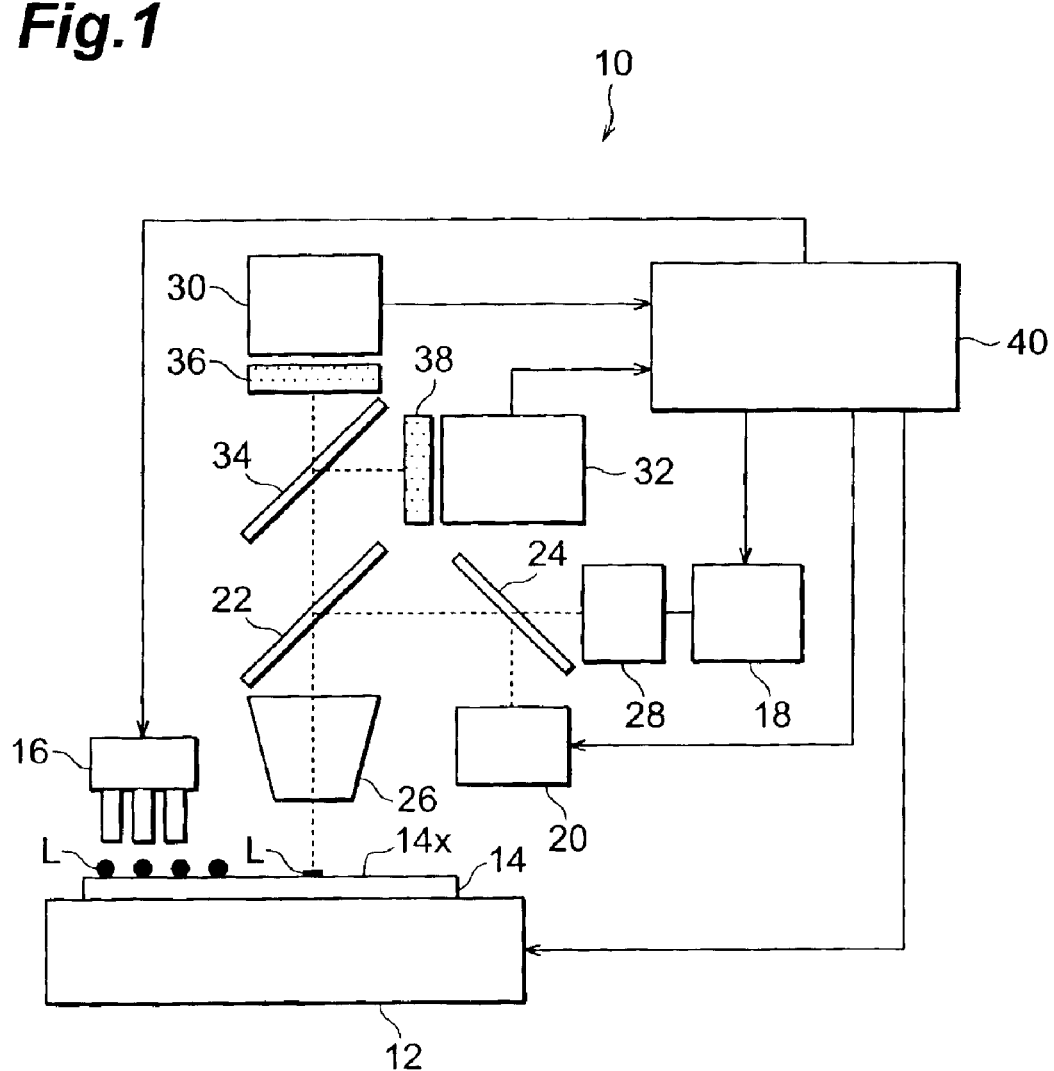
FIG. 1 is a diagram, showing a liquid-contained substance analysis device of a first embodiment.
Figure 2:
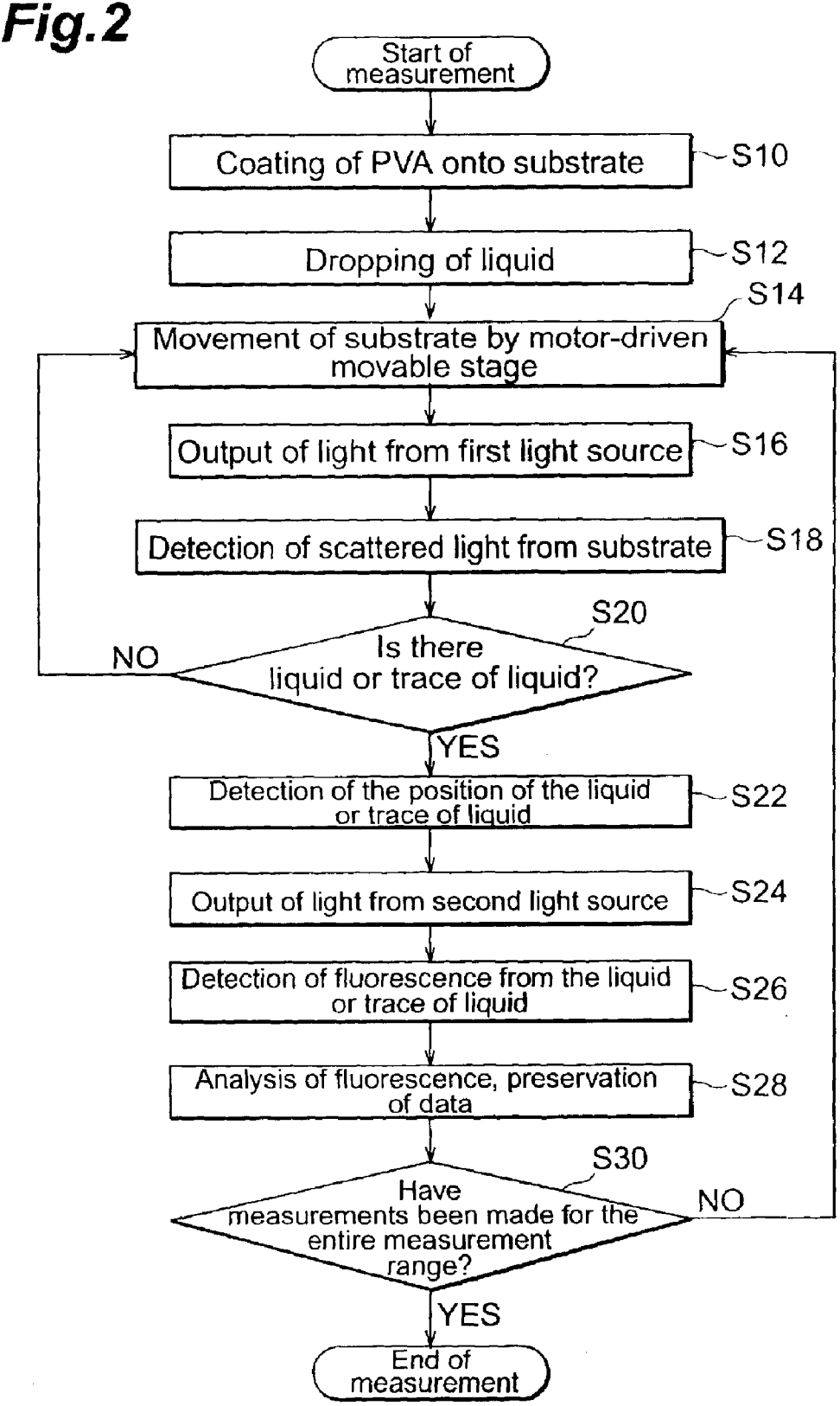
FIG. 2 is a flowchart, showing the operations of the liquid-contained substance analysis device of the first embodiment.

FIG. 1 is a diagram, showing the arrangement of a liquid-contained substance analysis device (referred to hereinafter as "analysis device") 10. Analysis device 10 comprises a motor-driven movable stage 12, a substrate 14, set on motor-driven movable stage 12, a liquid dropper 16 for dropping a liquid L to be analyzed onto substrate 14, and a first light source 18 and a second light source 20, each of which illuminates light onto substrate 14 and the liquid L that has been dropped onto substrate 14.

Substrate 14, which is set on motor-driven movable stage 12, is mirror finished. Light that is perpendicularly incident on substrate 14 is thus reflected in the direction perpendicular to substrate 14. The surface of substrate 14 is also coated with a water-soluble thin film 14x.

Thin film 14x is formed of a water-soluble organic thin film, in particular, water-soluble PVA (polyvinyl alcohol).

First light source 18 is positioned to output light substantially parallel to the substrate plane. A first half-mirror 22, is positioned along the output optical axis of first light source 18 and is tilted by 45° with respect to the optical axis. The output light from first light source 18 is thereby bent at a right angle in the direction of substrate 14. The output light bent by first half-mirror 22 is illuminated onto substrate 14. An objective lens 26 is disposed between first half-mirror 22 and substrate 14, and the output light from first light source 18 is illuminated onto a predetermined region (hereinafter, this predetermined region shall be referred to as "measurement spot") R on substrate 14 by means of objective lens 26.

Objective lens 26 is preferably a dark-field lens. This is because with a dark-field objective lens 26, the illuminated light will be illuminated onto substrate 14 at an angle with respect to the substrate normal and the reflected light (from the substrate) that is directed in the substrate normal direction will thereby be reduced to enable a scattered light image of high contrast to be obtained. A focal depth adjustment optical device 28 is disposed along the output optical axis at a position near first light source 18 to provide an arrangement that enables the first and second light of different wavelengths to be adjusted to be equal in focal depth.

Second light source 20 is a light source that outputs light of a shorter wavelength than first light source 18 and is an excitation light source for generation of fluorescence from liquid L. Second light source 20 outputs light substantially perpendicular to substrate 14 and is disposed so that its optical axis intersects the optical axis of the output light from first light source 18. At the position at which the output light from second light source 20 and the output light from first light source 18 intersect, a second half-mirror 24 is disposed in a manner that is tilted by 45° with respect to the output optical axis of second light source 20, and the output light from second light source 20 is thereby bent and made to progress along the same optical axis as the output light from first light source 18 and reach measurement spot R on substrate 14.

Motor-driven movable stage 12 can move substrate 14 so that substantially the entire region of substrate 14 can be scanned by means of measurement spot R. Also, liquid dropper 16, for dropping liquid L, which is the subject of measurement, is disposed above motor-driven movable stage 12, and motor-driven movable stage 12 can move substrate 14 to a position at which liquid L is to be dropped by liquid dropper 16.

Analysis device 10 comprises a light detector 30, which detects scattered light resulting from the scattering, by the liquid L or trace of the liquid L that exists on substrate 14, of light output from first light source 18 and illuminated onto substrate 14, and a fluorescence detector 32, which detects the fluorescence emitted from the liquid L as a result of the light output from second light source 20 and illuminated onto the liquid L that has been dropped onto substrate 14.

Light detector 30 detects the scattered light scattered by the liquid L or a trace of the liquid L that exists on substrate 14. Light detector 30 is disposed above substrate 14 so as to lie along the same straight line as substrate 14 and objective lens 26. An optical filter 36, for cutting light from the exterior, is disposed in front of the light detection surface of light detector 30. Between first half-mirror 22 and optical filter 36, a half-mirror 34 is disposed in a manner that is tilted by 45° with respect to the normal to the substrate plane and splits the light from substrate 14 into a direction perpendicular to the optical axis.

Fluorescence detector 32 is disposed along the optical axis of the split light. Fluorescence detector 32 detects the fluorescence emitted by excitation of substances contained in liquid L as a result of light output from second light source

20. Also, an optical filter 38, for cutting the reflected light of the excitation light output from second light source 20, is disposed in front of the light detection surface of fluorescence detector 32.

Analysis device 10 furthermore has a computer 40. Computer 40 is connected to first light source 18, second light source 20, motor-driven movable stage 12, and liquid dropper 16 and controls the respective operations of these components. Computer 40 is also connected to light detector 30 and fluorescence detector 32, has the function of performing image processing and data analysis based on the light detected by the respective detectors 30 and 32, and thus functions as a position detector and as an analyzer.

The operations of analysis device 10 shall now be described, and in accompaniment, a liquid-contained substance analysis method of this embodiment shall be described. In the description that follows, the range onto which liquid L to be analyzed is dropped, that is the range in which there is a possibility that liquid L or a trace of liquid L exists on substrate 14 shall be referred to as the "measurement range."

First, substrate 14, which has been mirror finished, is coated with a thin film 14x (S10) and set on the upper surface of motor-driven movable stage 12. Substrate 14 is then moved by motor-driven movable stage 12 so that the measurement range will be set at the position onto which liquid L will be dropped by liquid dropper 16. Subsequently, a microvolume of liquid L is dropped onto substrate 14 by means of liquid dropper 16 (S12).

Substrate 14 is then moved by motor-driven movable stage 12 so that measurement spot R will be contained within the measurement range (S14). Motor-driven measurement stage 12 is stopped once, light from first light source 18 is output, and light is illuminated onto measurement spot R of substrate 14 (S16). The scattered light that is scattered by the liquid L or the trace of the liquid L that exists on substrate 14 is then detected by light detector 30 (S18).

Based on the result of detection by light detector 30, it is judged whether or not liquid L or the trace of liquid L exists within measurement spot R of substrate 14 (S20). This judgment is made based on whether or not scattered light has been detected. That is, since substrate 14 is mirror-finished, the illumination light from first light source 18 will not be scattered by substrate 14.

Thus if scattered light is detected, it is judged that either liquid L or a trace of liquid L exists on substrate 14. If liquid L exists on substrate 14, light illuminated onto substrate 14 is scattered by this liquid L since liquid L acts as a mirror. Even if liquid L has evaporated, since thin film 14x, which had been coated onto the surface of substrate 14 dissolves and the surface of substrate 14 is thereby modified when liquid L is dropped, a trace of liquid L will remain and the light illuminated by substrate 14 will thereby be scattered.

If as a result of judgment, it is judged that liquid L or a trace of liquid L exists, the scattered light is analyzed by computer 40 to detect the position of liquid L (S22) That is, if liquid L exists, since the illuminated light will be scattered by liquid L itself, the position of liquid L can thereby be detected. Also, even if liquid L has evaporated, since the surface of substrate 14 that has been modified by the dropped liquid L bulges so as to surround the location at which liquid L had existed, the position onto which liquid L had been dropped can be detected by analysis of the scattered light.

Figure 3A:
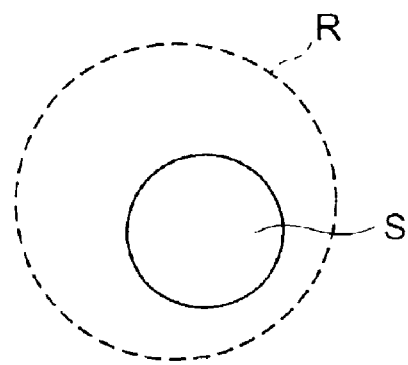
FIGS. 3A, 3B, 3C, and 3D are diagrams, showing images of the scattered light and fluorescence in the liquid-contained substance analysis device of the first embodiment.
Figure 3B:
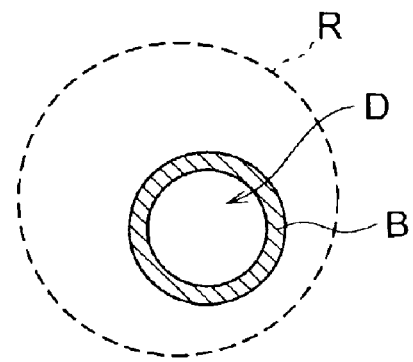

FIGS. 3A and 3B illustrate specific examples. FIG. 3A is a diagram, showing an image of scattered lights detected by light detector 30. By analyzing this scattered light S by means of computer 40, an outline (liquid L trace) B on the surface of substrate 14 that has been modified by the dropped liquid L can be determined as shown in FIG. 3B. In this case, the position D onto which liquid L has been dropped is at the inner side of outline B.

On the other hand, if it has been judged that neither liquid L nor a trace of liquid L exists, the step (S14) of moving substrate 14 by means of motor-driven movable stage 12 is returned to. Here, in order so that the entire measurement range of substrate 14 may be covered by means of measurement spot R, substrate 14 is moved so that the measurement spot R after movement of substrate 14 will be adjacent to the measurement spot R onto which light was illuminated previously.

Figure 3C:
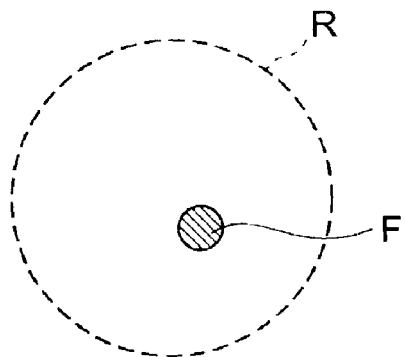
Figure 3D:
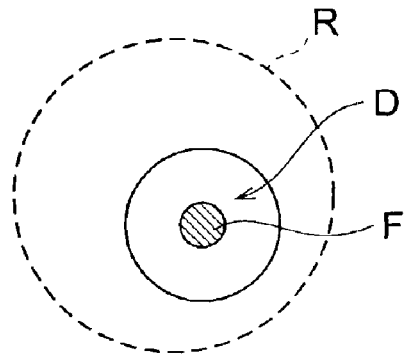

After the position of liquid L or of a trace of liquid L has been detected, light from second light source 20 is output and illuminated onto the detected position D (S24). As shown in FIG. 3B, detected position D lies at the inner side of outline B. The fluorescence that has been excited by liquid L or trace of liquid L is then detected by fluorescence detector 32 (S26). An image of the detected fluorescence F is shown in FIG. 3C.

Since the fluorescence F that arises as a result of excitation of substances contained in liquid L will exist at the position at which liquid L or trace of liquid L has been detected as shown in 3D, in a case where the substances contained liquid L are to be analyzed, excitation light is illuminated onto the range of the detected position D and studied. The fluorescence that has been detected by fluorescence detector 32 is then analyzed and the analysis results are preserved by means of computer 40 (S28).

Subsequently, analysis device 10 judges whether or not measurements have been made for the entire measurement range (S30), and if measurements have been made for the entire measurement range, the measurements are ended. If measurements have not been made for the entire measurement range, the step of moving substrate 14 by means of motor-driven movable stage 12 is returned to again (S14).

Since analysis device 10 of this embodiment has a first light source 18, which illuminates light onto a mirror-finished substrate 14, and a light detector 30, which detects the scattered light scattered by liquid L or a trace of liquid L that exists on substrate 14, if liquid L exists on substrate 14 even by a minute amount, the position of liquid L or trace of liquid L can be specified based on the detected scattered light. Analysis of an extremely minute amount of liquid L can thus be carried out smoothly.

Also with analysis device 10 of this embodiment, since a thin film 14x is coated onto the surface of substrate 14 and when liquid L is dropped, thin film 14x dissolves and the surface of substrate 14 is thereby modified, even if liquid L evaporates, the light illuminated by first light source 18 will be scattered and the position on to which liquid L has been dropped can be detected by means of this scattered light.

Also with analysis device 10 of this embodiment, since first light source 18, which illuminates light for detection of the position of liquid L, uses light that is longer in wavelength than the light of second light source 20, the liquid L that is subject to analysis will not be destroyed.

With the liquid-contained substance analysis method of this embodiment, since liquid L, which is to be analyzed, is dropped onto a mirror-finished substrate 14 and the position of liquid L on substrate 14 is detected by illumination of light onto substrate 14 and analyzing the scattered light due to liquid L or trace of liquid L that exists on substrate 14, the position of liquid L can be detected even if it is extremely minute in amount. Analysis of an extremely minute amount of liquid L can thus be carried out smoothly.

Figure 4:
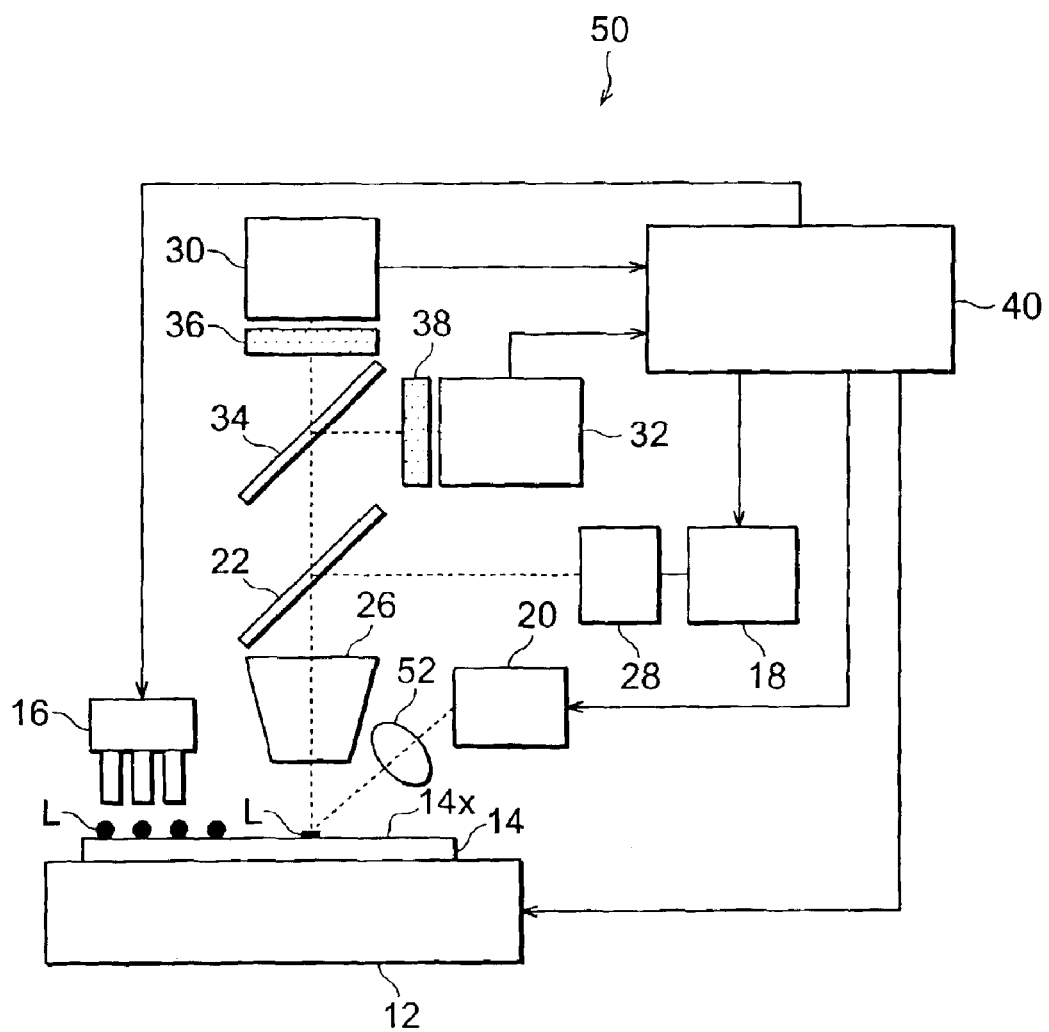
FIG. 4 is a diagram, showing a liquid-contained substance analysis device of a second embodiment.

An analysis device 50 of a second embodiment of this invention shall now be described. FIG. 4 is a diagram, showing analysis device 50 of the second embodiment.

Though analysis device 50 of the second embodiment is the same in basic arrangement as analysis device 10 of the first embodiment, it differs in that second light source 20 is disposed so that light is illuminated from a direction that intersects the normal to the substrate plane. A lens 52 is disposed along the optical axis of the output light from second light source 20 to form an optical system for illuminating light onto a measurement spot R on a substrate 14.

The operations of analysis device 50 of the second embodiment are the same as the operations of analysis device 10 of the first embodiment.

In addition to providing the same effect as analysis device 10 of the first embodiment that the position of liquid L that has been dropped onto substrate 14 can be detected smoothly, analysis device 50 of the second embodiment provides the following effect.

That is, with analysis device 50, excitation light is made incident from a direction that intersects the normal to the substrate plane and the fluorescence that is emitted as a result of this excitation light is detected by a fluorescent detector disposed in the direction of the normal to the substrate plane. Since the reflected light of the excitation light will therefore not enter fluorescence detector 32 directly, the fluorescence emitted from liquid L can be detected even if it is weak.

Though embodiments of this invention have been described in detail above, this invention is not limited to the above-described embodiments.

Though with the above-described embodiments, a substrate 14, which was coated on the surface with a thin film 14x formed of PVA, was used, a silicon substrate 14, 25 having a silicon oxide film (natural oxidation film) as thin film 14x, may be used instead.

With such an arrangement, when a liquid is dropped onto silicon substrate 14, a thin film 14x, comprising silicon oxide, forms at the location onto which the liquid was dropped, thus enabling a so-called "watermark" to be left as a trace of liquid L on the silicon substrate and thus even if the liquid evaporates, the trace thereof can be detected.

Figure 5A:
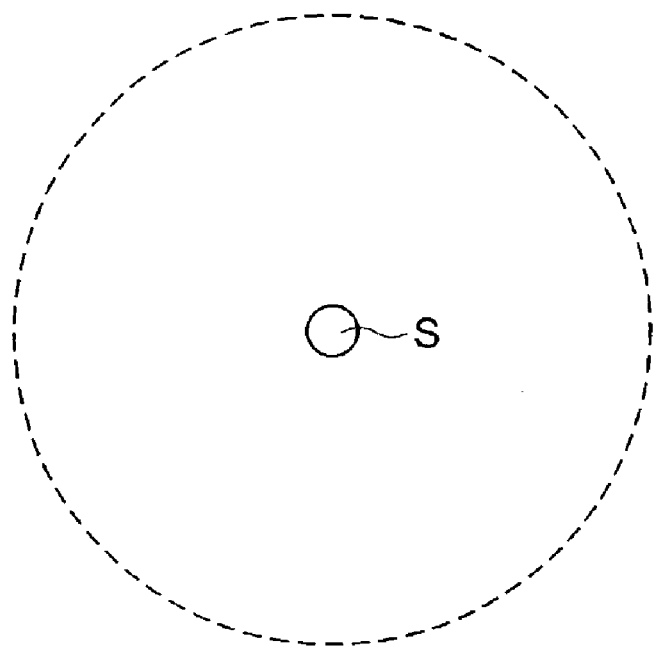
FIGS. 5A and 5B are diagrams, showing images of the scattered light and fluorescence in a case where a silicon substrate is used.
Figure 5B:
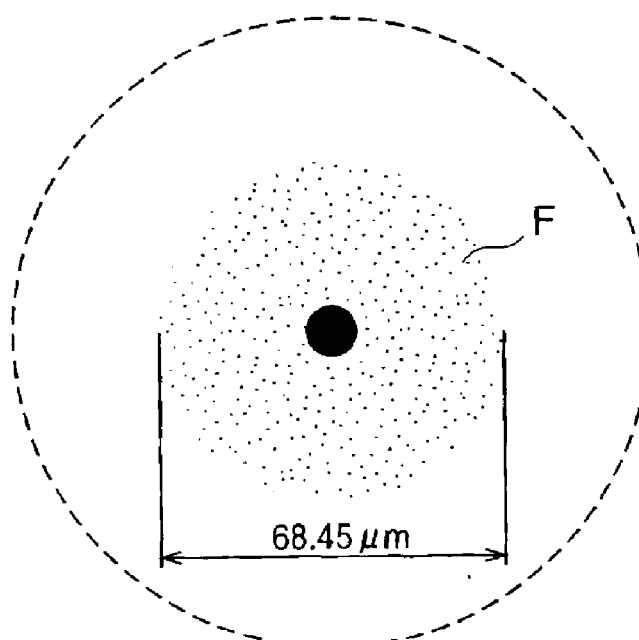

FIG. 5A is a diagram, showing the image of scattered light when a silicon substrate is used, and FIG. 5B is a diagram, showing the image of fluorescence in the same case. As can be understood from FIGS. 5A and 5B, when silicon substrate 14 is used, since the range in which fluorescence F can be observed will be greater than the range in which scattered light S can be observed, a range within a fixed radius centered about scattered light S must be set as the analysis range. The magnitude of this radius is determined by the diameter of the liquid drop formed by the extremely minute amount of the liquid, and, for example, when the liquid drop diameter is 70 $\mu$m, the analysis range is preferably set to be within a radius of 35 to 40 $\mu$m centered about scattered light S.

Also though with the above-described embodiments, substrate 14 is moved by means of motor-driven movable stage 12 to make measurement spot R be scanned over the entire measurement range of substrate 14, light maybe illuminated over the entire measurement range or over a part of the measurement range (over a range wider than measurement spot R) of substrate 14 and a plurality of positions onto which liquid has been dropped may be detected in a batch by means of scattered light scattered by liquid L or traces of liquid L on substrate 14.

Such an arrangement for batch analysis can be realized by expanding the illumination range of the output light from each of first light source 18 and second light source 20 to cover the entire measurement range and likewise expanding the detection range of each of light detector 30 and fluorescence detector 32 to cover the entire measurement range. FIGS. 6A, 6B, 6C, and 6D are diagrams, showing an example where the measurement range of substrate 14 is analyzed in a batch.

Figure 6A:
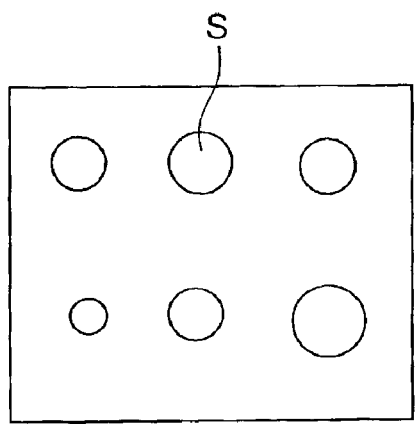
FIGS. 6A, 6B, 6C, and 6D are diagrams, showing images of the scattered light and fluorescence in a case where fluorescence analysis is performed in a batch.
Figure 6C:
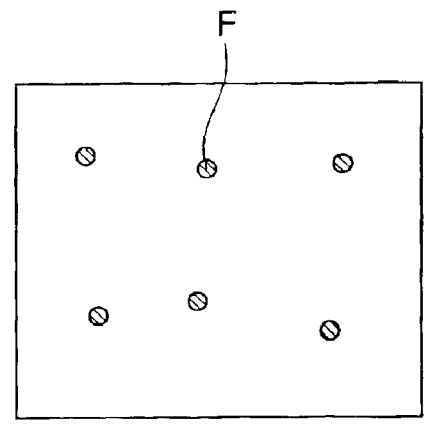
Figure 6B:
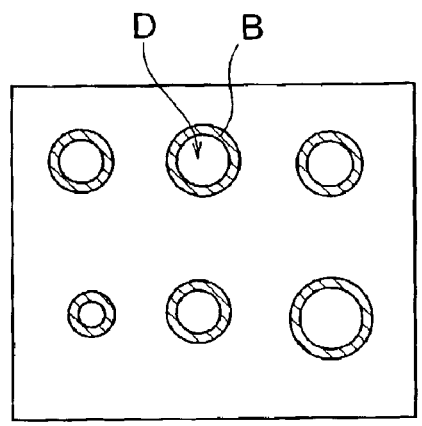
Figure 6D:
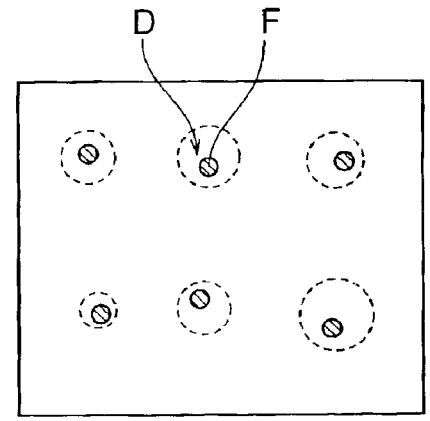

By illuminating light across the entire measurement range, acquiring the resulting scattered light S by light detector 30 as shown in FIG. 6A, and analyzing this scattered light by means of computer 40, the outlines B of liquid drop traces such as shown in FIG. 6B, are determined to detect the positions of liquid L within the measurement range. By then illuminating the entire measurement range with excitation light, fluorescence F is acquired in the manner shown in FIG. 6C. The results of the analysis using fluorescence F can then be cut out in accordance with the positional relationship shown in FIG. 6D. By thus performing batch analysis of substances contained in a liquid, the work efficiency can be improved.

INDUSTRIAL APPLICABILITY

This invention can be applied to a liquid-contained substance analysis device and a liquid-contained substance analysis method.

What is claimed is:

1. A liquid-contained substance analysis device comprising:
    a mirror-finished substrate, onto which a liquid that is to be analyzed is dropped;
    a first light source for illuminating said substrate;
    a light detector, detecting scattered light resulting from the scattering of light from said first light source by said liquid or trace of said liquid that has been dropped onto said substrate;
    a position detector, detecting the position on to which said liquid has been dropped based on said scattered light detected by said light detector;
    a second light source, illuminating the position detected by said position detector with light of a shorter wavelength than the light output from said first light source;
    a fluorescence detector, detecting fluorescence resulting from the excitation of said liquid or trace of said liquid by the light that has been illuminated from said second light source; and
    an analyzer, analyzing substances contained in said liquid by the fluorescence detected by said fluorescence detector.

2. The liquid-contained substance analysis device as set forth in claim 1, wherein said second light source is positioned so that the output light from said second light source intersects the normal to the plane of said substrate plane and said fluorescence detector is positioned in the direction of the normal to said substrate plane.

3. The liquid-contained substance analysis device as set forth in claim 1, wherein the surface of said substrate is coated with a water-soluble organic thin film.

4. The liquid-contained substance analysis device as set forth in claim 1, wherein a silicon oxidation film is formed on the surface of the substrate.

5. The liquid-contained substance analysis device as set forth in claim 1, further comprising a stage for setting said substrate thereon and moving said substrate so that light from said first light source will be illuminated onto said substrate.

6. A liquid-contained substance analysis method comprising:

a liquid dropping step of dropping a liquid to be analyzed onto a mirror-finished substrate.

a light illumination step of illuminating light unto said substrate by means of a first light source.

a scattered light detection step of detecting scattered light resulting front the scattering of light from said first light source by said liquid or trace of said liquid that has been dropped onto the substrate in said dropping step:

a position detection step of detecting the position onto which said liquid has been dropped based on said scattered light detected in said scattered light detection step;

a second light illumination step of illuminating the position detected in said position detection step with light from a second light source that outputs light of a shorter wavelength than the light output from said first light source.

a fluorescence detection step of detecting the fluorescence resulting from the excitation of said liquid or trace of said liquid by the light illuminated in said second light illumination step: and an analysis step of analyzing substances contained in said liquid based on the fluorescence detected in said fluorescence detection step.

* * * * *